US007083964B2

(12) United States Patent
Kurfürst et al.

(10) Patent No.: US 7,083,964 B2
(45) Date of Patent: Aug. 1, 2006

(54) METHOD FOR PURIFYING ENZYMES FROM CLOSTRIDIUM HISTOLYTICUM USING MULTI-STAGE CHROMATOGRAPHY

(75) Inventors: Manfred Kurfürst, Moorrege (DE); Stefan Schmidbauer, Lahntal (DE)

(73) Assignee: Nordmark Arzneimittel GmbH & Co. KG, Uetersen (DE)

( * ) Notice: Subject to any disclaimer, the term of this patent is extended or adjusted under 35 U.S.C. 154(b) by 156 days.

(21) Appl. No.: 10/478,545

(22) PCT Filed: Jun. 1, 2002

(86) PCT No.: PCT/EP02/05021
§ 371 (c)(1),
(2), (4) Date: Nov. 21, 2003

(87) PCT Pub. No.: WO03/004628
PCT Pub. Date: Jan. 16, 2003

(65) Prior Publication Data
US 2004/0137596 A1 Jul. 15, 2004

(30) Foreign Application Priority Data
Jul. 2, 2001 (DE) ........................................ 101 31 994
Jul. 14, 2001 (DE) ........................................ 101 34 347

(51) Int. Cl.
*C12N 9/48* (2006.01)

(52) U.S. Cl. .................... 435/212; 435/183; 424/94.67; 424/94.65; 424/94.63; 424/94.6; 210/634; 210/656; 210/667

(58) Field of Classification Search .............. 424/94.67, 424/94.65, 94.63, 94.6; 435/183, 212; 210/634, 210/656, 667
See application file for complete search history.

(56) References Cited

U.S. PATENT DOCUMENTS 5,332,503 A 7/1994 Lee et al.
5,853,976 A * 12/1998 Hesse et al. ................... 435/4

OTHER PUBLICATIONS

Porter et al, J Biol Chem, 1971, vol. 246, No. 24, pp. 7675–7682.*
Bio–Rad Laboratories, Catalog Index "CHT Ceramic Hydroxyapatite" and "Bio–Gel Hydroxyapatite HT and HTP" accessed Sep. 28, 2004 www.bio–rad.com.*
Bio–Rad Bulletin2156,"Chromatography: CHT Ceramic Hydroxyapatite– A New Dimension in Chromatography of Biological Molecules" accessed Sep. 30, 2004 www.bio–rad.com/LifeSciences/pdf/Bulletin_2644.pdf.*
Merriam–Webster On–line Dictionary, accessed Oct. 7, 2004, www.m–w.com.*
Nash D C et al, "Modification of Polystyrenic Matrices for the Purication", BD. 758, No. 1, Jan. 10, 1997, pp. 53–64.

(Continued)

*Primary Examiner*—Leon B. Lankford, Jr.
*Assistant Examiner*—Allison M. Ford
(74) *Attorney, Agent, or Firm*—Friedrich Kueffner

(57) ABSTRACT

The invention relates to a method for purifying at least one enzyme obtained in an excess fermentation of *Clostridium histolyticum*.

It is provided for that the enzymes of the excess fermentation are separated by a multistage chromatography method by exclusively using chromatography materials on styrene/divinyl-benzene base and/or on base of in particular ceramic hydroxylapatite.

20 Claims, 1 Drawing Sheet

OTHER PUBLICATIONS

Kloeck Gerd et al "Fractions From Commercial Collagenase Preparations . . . " Cell Transplantation, BD. 5, No. 5, 1996, pp. 543–551.

Bond M D et al: "Purification and Separation of Individual Collagenases . . . " Biochemistry, BD. 23, No. 13, 1984, pp. 3077–3085.

Rounds M A et al: Poly (Styrene–Divinylbenzene) –Based Strong Anion–Exchange Netherlands, Jun. 1987, BD. 397, Jun. 6, 1987, pp. 25–38.

Leonard M et al: "Polyvinyl Alcohol–Coated Macroporous Polystyrene . . . " Biomedicalapplications, BD. 664, No. 1, 1995, pp. 39–46.

* cited by examiner

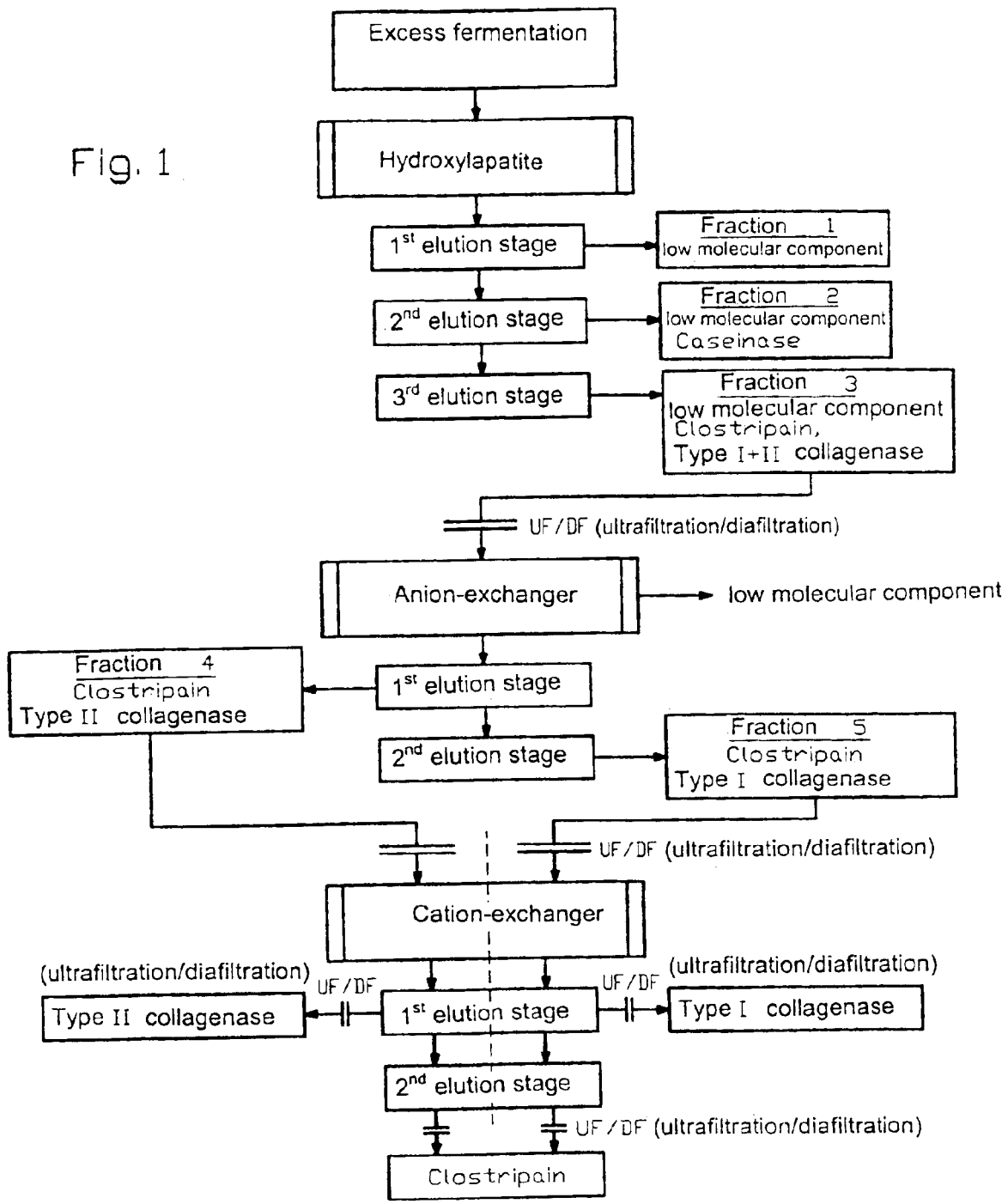

METHOD FOR PURIFYING ENZYMES FROM CLOSTRIDIUM HISTOLYTICUM USING MULTI-STAGE CHROMATOGRAPHY

FIELD OF APPLICATION

The invention relates to a method for purifying at least one enzyme contained in an excess fermentation of *Clostridium histolyticum* and an enzyme produced according to this method as well as the use thereof.

PRIOR ART

The bacterium *Clostridium histolyticum* constitutes, when cultivated in a peptone containing nutrient medium extracellularly a complex enzyme mixture which contains collagenases, different proteolytic enzymes as well as low molecular weight constituents. Type 1 and type 11 collagenases (clostridiopeptidase A, EC 3.4.24.3) with molecular weights in the range of 65 to 125 kD and isolectric points between 5 and 6.5 have been described as main constituents (Bond, van Wart; Biochemistry, 1984, 23, 3077–3085). Further main constituents are the SH-protease clostripain occuring as a heterodimer (clostridiopeptidase B, EC 3.4.22.8) with a molecular weight of approximately 59 kD and the poorly characterized so-called neutral protease (caseinase) with a molecular weight of 34.5 kD determined by MALDI-TOF.

Collagenases are enzymes which cleave peptide bonds of the fiber proteine collagen. They are used in biochemistry and medicine, for example in order to isolate cells or cell bonds of tissues. Type I and type II collagenases differ in their activity with respect to high molecular collagen and small synthetic substrates. While type I collagenases preferably cleave high molecular collagen, type II collagenases react mainly with synthetic substrates such as, for example Pz-Pro-Leu-Gly-Pro-D-Arg (Wünsch, Heidrich; Z. Physiol. Chem. 333, 1963, 149–151), His-Pro (Nordwig, Wünsch; Z. Physiol. Chem. 316, 1959, 287) or Phe-Ala-Leu-Gly-Pro-Ala (van Wart, Steinbrink; Anal. Giochem. 113, 1981, 356–365). Both collagenase types can also be unequivocally differentiated by reversed phase chromatography (RPC).

The U.S. Pat. No. 5,332,503 describes a method for the chromatographic purification of collagenase of *Clostridium histolyticum*. This chromatography method comprises, among others, a gel filtration step as well as a dyestuff/ligand affinity chromatography by using reactive red agarose gel. The method shows decisive disadvantages for producing collagenases for pharmaceutical purposes under GMP conforming conditions. So, the reactive red agarose gel used in the method involves the risk of a so-called bleeding of the chromatography material and of related toxicological problems. Furthermore, gel filtration steps are fundamentally time consuming and expensive and offer less efficient cleaning-in-place (CIP) possibilities. This makes the use of this method difficult at a commercial scale. Moreover, the method requires the use of detergents so that high expenses are necessary for the purification validation and undesired changes of the end product can be caused. Finally, the method does not allow a separation of the type I and type 11 collagenases.

From the documents U.S. Pat. No. 5,830,741 and U.S. Pat. No. 5,952,215, we know a purification method for the separation of type I and type 11 collagenases which comprises a dyestuff/ligand affinity chromatography, a cation-exchange chromatography and an anion-exchange chromatography. Here also, there is the risk of bleeding of the dyestuff used in the affinity chromatography. Furthermore, the chromatography materials used allow only relatively low flow rates. Moreover, all the chromatographic steps take place by gradient elution, whereby the enzymes bound to the chromatography materials are eluted by linear salt concentration and/or pH gradients. As for the result, the known method is thus extremely time consuming.

Aim, Solution, Advantage

Against this background, the aim of this invention is to make available a method for separating and purifying at least one extracellular main enzyme of *Clostridium histolyticum* which overcomes the described disadvantages of the prior art.

This aim is achieved by a method according to the present invention. A very quick and cost-saving enzyme purification can be realized in that the enzymes of the excess fermentation of *Clostridium histolyticum* are separated by a single-stage or preferably a multiple-stage chromatography method by exclusively using chromatography materials on a styrene/divinylbenzene base and/or on the base of ceramic hydroxylapatite, whereby high purity enzymes are obtained which are appropriate in particular for use in pharmacy and/or biochemistry because of the absence of toxicologically dangerous substances. This method does not need any product contacting steps, which makes its use in the pharmaceutical field particularly advantageous. It can be used for the production of sterile collagenase enzymes. By styrene/divinyl benzene, a copolymer is understood which consists of polystyrene cross-linked with divinyl benzene. Through the substitution of this base matrix with the most different functional groups, a bond of proteins to the material and thus a separation thereof is made possible. Depending on the choice of the functional group, different bond and separating mechanisms, for example cation-exchange or ion-exchange mechanisms, can be used. On the other hand, with hydroxylapatite the matter is of a phosphate of calcium of the total formula $Ca_{10}(PO_4)_6(OH)_2$ which allows a protein bond because of ionic electrostatic interactions as well as a stronger ionic complex bond. However, in detail the bond mechanism of proteins to hydroxylapatite has not been yet understood.

The chromatography materials used allow the adjusting of high flow rates with good separating properties so that there result very short purification times. This is particularly valid if, according to a preferred embodiment of the invention, sintered, thus ceramic hydroxylapatite is used. The use of ceramic hydroxylapatite has the advantage, compared to non-sintered (crystalline) hydroxylapatite, that the material can be produced reproduceably and because of its porous structure only very low back pressures are generated so that the risk of column damages is minimized and high linear flow rates are made possible. The elution from sintered hydroxylapatite material is carried out preferably at flow rates of at least 200 cm/h, in particular of at least 300 cm/h. In the case of the polymer styrene/divinylbenzene material, flow rates of at least 500 cm/h are even preferred, in particular of at least 1000 cm/h. In this way, the processing times can be considerably reduced compared to known methods.

A further processing time reduction as well as a simplification of the process expenditure is achieved in that at least one chromatography stage, preferably all chromatography stages, is carried out as a stepwise elution. Compared with a gradient elution, elution means and thus expensive buffer substances can thus be saved. Moreover, the generation of a gradient is a problem on the process scale.

According to an advantageous configuration of the invention, the chromatography materials are selected in such a way that the individual chromatographic steps are based exclusively on electrostatic interactions and/or on an ion bond and/or an ion complex bond. Particularly advantageously, the method comprises at least one anion-exchange chromatic stage and/or at least one cation-exchange chromatic stage and/or at least one hydroxylapatite chromatic stage. Particularly good results have been obtained in a three-stage chromatography method, whereby a first stage is carried out on sintered hydroxylapatite material, a second stage on an anion-exchange material on a styrene/divinylbenzene base and a third chromatographic stage on a cation-exchange material on a styrene/divinylbenzene base, preferably in said order; however, other orders are also possible; the number of stages can vary as well.

Preferably, the method according to the invention thus does not comprise any time consuming and cost intensive gel filtration steps so that the risk of a self-digesting of enzymes to be separated is minimized. Furthermore, the abandonment of gel filtrations makes possible the carrying out of the chromatographic stages in a wide temperature range between 4 and 25° C., thus also at ambient temperature. Moreover, the method does not comprise any affinity chromatographic stages so that the risk of bleeding, thus of washing out of the affinity ligands of the chromatography material does not exist. Finally, the method according to the invention does not provide any protein precipitation steps which can cause undesired protein structure changes. Furthermore, thus there results the advantage that no detergents or chaotropic substances (ammonium sulphate, polyethyleneglycol etc.) are used, the subsequent removing of which is always bound to a high process expenditure.

The chromatography materials used have the further advantage to be chemically inert to a wide extent and to be able to be purified with relatively highly concentrated alkaline lyes, for example with trimolar soda lye. This guarantees a very effective purification and thus a functional maintenance of the materials as well as a good reproducibility of the method. The high pressure stability of the chromatograhy materials further allows use in high pressure liquid chromatography methods (HPCL). Because of the absence of toxicologically dangerous, process induced substances such as, for example, affinity ligands or detergents, the proteins purified according to the invention, in particular type I and/or type II collagenase and/or clostripain and/or neutral protease (caseinase), can be used particularly advantageously for pharmaceutical or biochemical purposes.

Further preferred configurations of the invention result from the other characteristics indicated in the subclaims.

Furthermore, the invention relates to an enzyme purified according to the inventive method, as well as the use of an enzyme produced according to the inventive method.

SHORT DESCRIPTION OF THE DRAWING

FIG. 1: A flow chart depicting the steps of the method of the invention.

DETAILED DESCRIPTION OF THE INVENTION AND BEST WAY OF CARRYING OUT THE INVENTION

After the cultivation of *Clostridium histolyticum* has taken place in a fermentation medium of animal or vegetable origin, the cells and other non soluble constituents are separated from the excess fermentation, for example by centrifugation or filtration. The excess fermentation which contains type I and type II collagenases, clostripain and caseinase as main constituents can be upgraded in the usual way before the chromatographic separation of these proteins.

The excess fermentation is pumped in a first step of the method onto a chromatography column filled with ceramic hydroxylapatite material of type I or type II (CHT), whereby said enzymes bind with the hydroxylapatite besides different other components. At temperatures of 4 to 25° C. and a pH-value of 6 to 9, the elution takes place as a stepwise elution with linear flow rates >300 cm/h. A phosphate buffer which contains 0 to 1000 mM of an alkali halide is convenient, whereby the phosphate concentration is gradually increased from 10 to 350 mM phosphate. Alternatively or additionally, the pH value of the buffer can be gradually increased from 6 to 9. Preferably three elution stages are carried out. The fraction 1 obtained in the first elution stage contains exclusively low molecular weight constituents. The fraction 2 of the second elution stage contains, besides low molecular weight components, neutral protease (caseinase). The fraction 3 of the third elution stage also contains low molecular weight components, the whole clostripain as well as all the type I and type II collagenases.

The fraction 3 will be desalted, for example, by ultrafiltration/diafiltration or nanofiltration or dialysis and eventually upgraded. Then, the desalted solution will be submitted to an anion-exchange chromatography in a second chromatographic step. A chromatography material on styrene/divinylbenzene base will be used for this and will be functionalized for example with a quaternary ammonium group. Thus, commercially available materials can be used (for example Source of the Pharmacia company, POROS of the PerSeptive company, Makroprep of the Biorad company). A separation of the cationic or nonionic low molecular weight constituents takes place already when loading the anion exchanger with the fraction 3. The elution of the bound constituents takes place at 4 to 25° C. in a buffered system in the pH range of 7 to 9.5 by stepwise elution with a linear flow rate above 500 cm/h, whereby an alkali halide or alkali-alkaline earth halide concentration gradually varies from 1 to 1000 mM and/or the pH value from 9.5 to 6. Preferably two fractions are separated, whereby the fraction 4 of the first elution stage contains clostripain and type II collagenase and the fraction 5 of the second elution stage also contains clostripain as well as type I collaqenase.

The fractions 4 and 5 are submitted to a cation-exchange chromatography in a third chromatographic stage separately from each other. For this, a column filling based on styrene/divinylbenzene material is also used which is, however, functionalized here with a cation binding group, for example S03H. The above mentioned commercial materials can also be used here. The elution of the cation-exchanger will be carried out at 4 to 25° C. in a buffered system in the pH range of 5.7 to 7 for linear flow rates of at least 500 cm/h with a stepwise elution. During the course of this, an alkali halide or alikali-alkaline earth halide concentration between 0 and 300 mM is gradually adjusted in the elution buffer and/or the pH value between 5 and 7. The elution is preferably carried out in two stages, whereby the respective collagenase is obtained in the first elution stage and clostripain in the second elution stage.

Embodiment

A culture of *Clostridium histolyticum* is fermented by using an animal or vegetable nutrient medium in liquid culture according to standard methods up to a desired cell density. After separation of the cells with usual methods, for example by centrifugation or filtration, 2000 mL of the concentrated excess fermentation are pumped with a linear flow rate of 300 cm/h onto a chromatography column filled with 1700 mL type I ceramic hydroxylapatite. The components bound to the hydroxylapatite column are eluted at 20 to 25° C. with a linear flow rate of 300 cm/h in three stages with a phosphate buffer, whereby the phosphate concentration is gradually increased. In the first elution stage, the elution takes place with approximately 10 CV (column volumes) with 10 mM phosphate buffer/100 mM NaCl are eluted with approximately 3 CV and the fraction 2 is obtained which contains caseinase and also low molecular weight components. For the third elution stage, 200 mM phosphate buffer/100 mM NaCl are eluted with approximately 5 CV. The fraction 3 collected in this way contains the enzymes clostripain and all the type I and type II collagenases. The fraction 2 is desalted and lyophilized. A separation of the low molecular weight constituents of caseinase can eventually be achieved with standard methods.

The fraction 3 is desalted by ultrafiltration/diafiltration or nanofiltration or dialysis and eventually upgraded. Then the fraction 3 is adjusted to a pH value of 9.0–9.3 with an appropriate buffer, for example 500 mM Tris pH 9.0–9.3. The buffered solution is pumped at 20–25° C. with a linear flow rate of approximately 1000 cm/h over a styrene/divinyl benzene column (POROS 50 PI of the PerSeptive company) functionalized as an anion-exchanger. The column is then washed with approximately 5 CV tris-buffer. The elution takes place at 20–25° C. and a linear flow rate of approximately 1000 cm/h in two elution stages with an increasing salt concentration. The fraction 4 is obtained by elution with 40 mM tris-buffer/6 mM CaCl2/30 mM NaCl pH 9.0–9.3 and contains the enzymes clostripain as well as type II collagenase. The fraction 5 which also contains clostripain as well as type I collagenase is obtained in the second elution stage by elution with 40 mM tris/6 mM $CaCl_2$/70 mM NaCl pH 9.0–9.3.

The fractions 4 and 5 are desalted for example by dialysis for 24 hours against 50 I $H_2O$ and adjusted with 50 mM MES buffer to a pH value of 5.9–6.1. Both fractions are chromatographed separately, the one from the other, on a cation-exchanger column on styrene/divinylbenzene material (for example POROS HS of the PerSeptive company). For this purpose, the fractions are loaded with a linear flow rate of approximately 700 cmlh at 20–25° C. onto the column and eluted under the same conditions. The elution of type II collagenase from fraction 4 or of type I collagenase from fraction 5 takes place respectively in a first elution stage with 10 mM MES buffer/20–40 mM NaCl pH 5.9–6.1 at 20–25° C. The clostripain containing solutions will be combined. All the solutions are desalted, dialyzed against 2 mM CaAc2 and then lyophilized.

A determination of the respective enzyme activities of the obtained enzymes took place according to known methods. Type II collagenase obtained by the method of the present invention has a specific activity of at least 13000 U/g, preferably at least 18000 U/g. Type I collagenase obtained by the method of the present invention has a specific activity of at least 3000 U/g, preferably at least 5000 U/g. Clostripain obtained by the method of the present invention has a specific activity of at least 200 U/mg, preferably at least 300 U/mg. Caseinase obtained by the method of the present invention has a specific activity of at least 1200 U/mg, preferably at least 1500 U/mg. (See Table). Furthermore the purity of the type I collagenase, type II collagenase, and clostripain has been determined by reverse phase chromatography to be at least 70%, preferably at least 80% (see Table). The results are summarized in the table below:

TABLE

|  | Activity | Purity[e] |
| --- | --- | --- |
| Type II collagenase | 18100 U/g[a] | Approx. 82% |
| Type I collagenase | 5180 U/g[b] | Approx. 85% |
| Clostripain | 322 U/mg[c] | Approx. 90% |
| Neutral protease | 1560 U/mg[d] |  |

[a]determined according to Wünsch E., Heidrich H.-G.; Z. Physiol. Chem. 333, 149–151, 1963;
[b]determined according to Doi, Shibata, Matoba; Anal. Biochem. 118, 173–184, 1981;
[c]determined according to Mitchel, Harrington; Methods Enzymol., 19, 635–642, 1970;
[d]determined according to Moore, Stein; Biol. Chem. 176, 367, 1948;
[e]determined according to RPC.

What is claimed is:

1. A method of purifying caseinase, type I collagenase, type II collagenase and clostripain produced in a medium by the fermentation of *Clostridium histolyticum*, comprising:
    a) substantially separating caseinase from the other three enzymes by exposing the medium to a sintered hydroxyapatite chromatographic material followed by eluting the enzymes at flow rates of at least 200 cm/h such that fractions are eluted comprising caseinase substantially separated from the other three enzymes and fractions are eluted which are substantially free of caseinase but contain the type I collagenase, type II collagenase and clostripain;
    b) substantially separating the type I and type II collagenases by exposing the fractions which are substantially free of caseinase but contain the type I collagenase, type II collagenase and clostripain to an anion-exchange chromatographic material with a styrene/divinylbenzene base and eluting the enzymes, at a flow rate of at least 500 cm/h, such that a fraction is eluted comprising type I collagenase and clostripain but substantially free of type II collagenase and a fraction is eluted comprising type II collagenase and clostripain but substantially free of type I collagenase; and
    c) separately exposing the type I collagenase/clostripain fraction and the type II collagenase/clostripain fraction to cation exchange chromatography and eluting the enzymes such that separate fractions are eluted comprising type I collagenase substantially free of clostripain, type II collagenase substantially free of clostripain and clostripain substantially free of either collagenase,
    wherein steps a), b) and c) are all carried out at between 4 and 25° C.

2. A method according to claim 1, wherein the method exclusively comprises separations which are based on electrostatic interactions and/or on ionic bonds and/or ion complex bonds.

3. A method according to claim 1, wherein at least one of the elutions is a stepwise elution.

4. A method according to claim 1, wherein the method comprises a first chromatographic stage on sintered hydroxylapatite material, a second chromatographic stage on an anion-exchanger material on sytrene/divinylbenzene base and eventually a third chromatographic stage on a cation-exchanger material on styrene/divinylbenzene base.

5. A method according to claim 1, wherein the elution in step a) is carried out at least 300 cm/h.

6. A method according to claim 1, wherein the elution in step b) is carried out at least 1000 cm/h.

7. A method according to claim 1, wherein the method does not comprise any protein precipation steps.

8. A method according to claim 1, wherein pressure stable chromatography materials are used.

9. A method according to claim 1, wherein the chromatography is carried out as column chromatography.

10. A method according to claim 1, wherein type II collagenase with a specific activity of at least 13000 U/g is obtained.

11. A method according to claim 1, wherein type I collagenase with a specific activity of at least 3,000 U/g is obtained.

12. A method according to claim 1, wherein clostripain with a specific activity of at least 200 U/mg is obtained.

13. A method according to claim 1, wherein caseinase with a specific activity of at least 1,200 U/mg is obtained.

14. A method according to claim 1, wherein type II collagenase and/or type I collagenase and/or clostripain are obtained with a purity of at least 70%.

15. A method according to claim 3, wherein all chromatography stages are carried out as stepwise elutions.

16. A method according to claim 10, wherein type II collagenase with a specific activity of at least 18000 U/mg is obtained.

17. A method according to claim 11, wherein type I collagenase with a specific activity of at least 5,000 U/g is obtained.

18. A method according to claim 12, wherein clostripain with a specific activity of at least 300 U/mg is obtained.

19. A method according to claim 13, wherein caseinase with a specific activity of at least 1500 U/mg is obtained.

20. A method according to claim 14, wherein type II collagenase and/or type I collagenase and/or clostripain are obtained with a purity of at least 80%.

* * * * *